(12) United States Patent
Molz, IV et al.

(10) Patent No.: US 7,094,240 B2
(45) Date of Patent: Aug. 22, 2006

(54) FLEXIBLE MEMBER TENSIONING INSTRUMENTS AND METHODS

(75) Inventors: Fred J. Molz, IV, Collierville, TN (US); Michael C. Sherman, Memphis, TN (US); Troy D. Drewry, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 226 days.

(21) Appl. No.: 10/339,837

(22) Filed: Jan. 10, 2003

(65) Prior Publication Data

US 2004/0138666 A1 Jul. 15, 2004

(51) Int. Cl.
*A61B 17/56* (2006.01)

(52) U.S. Cl. .......................... 606/74; 606/103
(58) Field of Classification Search .................. 606/74, 606/103, 105
See application file for complete search history.

(56) References Cited

U.S. PATENT DOCUMENTS

| | | | |
|---|---|---|---|
| 4,362,151 A * | 12/1982 | Cottrell ....................... 606/241 |
| 5,312,410 A * | 5/1994 | Miller et al. ................... 606/86 |
| 5,395,374 A | 3/1995 | Miller et al. |
| 5,540,698 A | 7/1996 | Preissman |
| 5,569,253 A * | 10/1996 | Farris et al. ................... 606/74 |
| 5,693,046 A * | 12/1997 | Songer et al. ................. 606/74 |
| 5,782,831 A | 7/1998 | Sherman et al. |
| 5,902,305 A * | 5/1999 | Beger et al. ................. 606/103 |
| 5,935,130 A | 8/1999 | Kilpela et al. |
| 5,935,133 A | 8/1999 | Wagner et al. |
| 5,964,769 A | 10/1999 | Wagner et al. |
| 6,053,921 A | 4/2000 | Wagner et al. |
| 6,146,386 A | 11/2000 | Blackman et al. |
| 6,378,289 B1 * | 4/2002 | Trudeau et al. ............. 606/103 |
| 6,391,030 B1 | 5/2002 | Wagner et al. |

* cited by examiner

*Primary Examiner*—Pedro Philogene
(74) *Attorney, Agent, or Firm*—Krieg DeVault LLP (57) ABSTRACT

An instrument for tensioning a flexible elongate member in a surgical procedure includes a tensioning mechanism engageable to a portion of the flexible elongate member and operable to apply a tensioning force to the elongate member. The instrument includes a distal end portion at a distal end of the tensioning mechanism that is adapted to allow orientation of the elongate member in a first direction for implantation and to allow the instrument to extend transversely to the implantation orientation during application of a tensioning force. The distal end portion can also include a receptacle to receive a structure at the surgical site to facilitate positioning of the distal end portion at the desired location.

35 Claims, 4 Drawing Sheets

FLEXIBLE MEMBER TENSIONING INSTRUMENTS AND METHODS

BACKGROUND

Several devices have been developed, for example, to tension cables in surgical applications. While such devices are useful, their application can be limited in minimally invasive surgical procedures, or in procedures where little space is provided at the operative site for positioning the device to apply a tensioning force. What is needed therefore, are instruments and methods having application in tensioning of elongate elements in minimally invasive surgical procedures and other procedures where space for positioning the instrument at the desired location may be obstructed.

SUMMARY

Instruments and methods for tensioning flexible elongate members are provided having application in minimally invasive surgical procedures. Also provided are instruments and methods for tensioning an elongate member having application at surgical sites with minimal space or obstructions that inhibit positioning and/or orientation of the tensioning instrument. The instruments and methods also have application in surgical procedures that are not minimally invasive and/or that have unobstructed surgical sites.

According to one aspect, there is provided an instrument for tensioning a flexible elongate member in a surgical procedure. The instrument includes a tensioning mechanism engageable to the flexible elongate member and operable to apply a tensioning force thereto for securement of the flexible elongate member to an anchor. The instrument includes a distal end portion at a distal end of the tensioning mechanism including a receptacle sized and shaped to at least partially receive a structure at the surgical site.

According to another aspect, an instrument for tensioning a flexible elongate member in a surgical procedure is provided. The instrument includes a tensioning mechanism engageable to a portion of the flexible elongate member and operable to apply a tensioning force to the elongate member. The instrument includes a distal end portion at a distal end of the tensioning mechanism. The distal end portion includes a support member contactable with the elongate member to orient in a first direction a portion of the elongate member extending from the support member away from the tensioning mechanism. The tensioning instrument is positionable relative to the elongate member so that the portion of the elongate member engaged with the tensioning mechanism is oriented in a second direction that is transverse to the first direction.

According to another aspect, a tensioning instrument includes a distal end portion having a support member. A flexible elongate member extends in an implantation orientation along the surgical site, and contacts the support member for extension in a direction transverse to the implantation orientation for engagement with the tensioning instrument.

According to a further aspect of the invention, a spinal stabilization system is provided that includes an anchor engageable to a spinal structure, a flexible elongate member engageable to the anchor for implantation along the spinal structure, and a tensioning instrument. The tensioning instrument is engageable to the flexible elongate member and operable to apply a tensioning force to the elongate member with a longitudinal axis of the tensioning instrument oriented transversely to implantation orientation of the elongate member.

According to another aspect, a method for tensioning a flexible elongate member in a surgical procedure includes engaging an anchor to bony structure in a patient; positioning a flexible elongate member through a portion of the anchor; securing the flexible elongate member to the patient; engaging the flexible elongate member to a tensioning instrument; positioning a distal end portion of the tensioning instrument about at least a portion of a structure adjacent the anchor; applying a tensioning force to the flexible elongate member; and securing the flexible elongate member to the anchor.

According to a further aspect, a method for tensioning a flexible elongate member in a surgical procedure includes engaging an anchor to a spinal structure; positioning a flexible elongate member through a portion of the anchor, the flexible elongate member extending in a first direction for implantation; securing the elongate member at a location spaced from the anchor; engaging the flexible elongate member to a tensioning instrument; positioning a distal end portion of the tensioning instrument adjacent the anchor; orienting a longitudinal axis of the tensioning instrument transversely to the first direction; and applying a tensioning force to the flexible elongate member.

These and other aspects are also discussed hereinbelow.

DESCRIPTION OF THE ILLUSTRATED EMBODIMENTS

For the purposes of promoting an understanding of the principles of the invention, reference will now be made to the embodiment illustrated in the drawings and specific language will be used to describe the same. It will nevertheless be understood that no limitation of the scope of the invention is thereby intended. Any such alterations and further modifications in the illustrated device, and any such further applications of the principles of the invention as illustrated herein are contemplated as would normally occur to one skilled in the art to which the invention relates.

Figure 1:
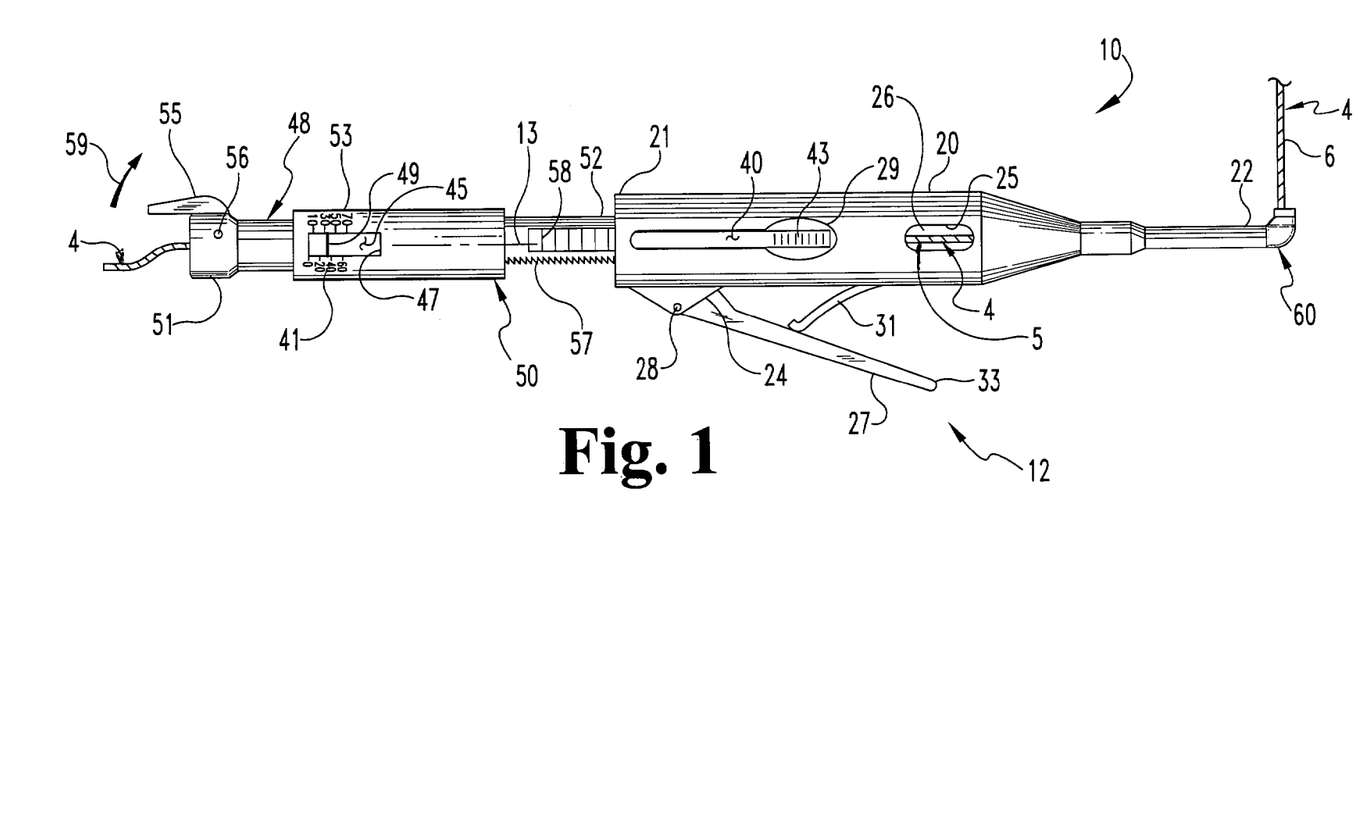
FIG. 1 is an elevation view of a tensioning instrument according to one aspect of the invention.

Referring now to FIG. 1, a surgical tensioning instrument 10 according to one aspect of the invention is shown for applying a tensioning force to elongate member 4. Tensioning instrument 10 include a proximal portion 12 and a distal end portion 60. Proximal portion 12 includes a mechanism by which a tensioning force can be applied to elongate member 4. Proximal portion 12 extends along a longitudinal axis 13. Elongate member 4 includes a first portion 5 extending generally along proximal portion 12, and a second portion 6 extending distally from instrument 10 that changes direction relative to proximal portion 12 as it exits distal end portion 60. Distal end portion 60, as shown in FIGS. 2–5, includes a passage 72 opening to one side of tensioning instrument 10 through which elongate member 4 extends in a direction transverse to the direction of proximal portion 12.

In use, tensioning instrument 10 can be employed in minimally invasive and other surgical procedures where it is not possible or desired that tensioning instrument 10 extend from the surgical site in the same general direction that second portion 6 of elongate member 4 extends along the surgical site. As such, elongate member 4 can be tensioned by employing a surgical approach with tensioning instrument 10 that is transverse to the direction which second portion 6 of elongate member 4 extends. In addition, tensioning instrument 10 can be placed adjacent the anchor to which a tensioned elongate member 4 is to be engaged. Distal end portion 60 can be provided with a receptacle 67 to at least partially receive a structure such as an anchor, implant or anatomical structure that might otherwise impede or inhibit positioning of tensioning instrument 10 at the desired location adjacent to the anchor to which elongate member 4 is to be engaged.

It is contemplated that elongate member 4 can be secured to any suitable anchor at the operative site. Examples of suitable anchors include bone screws, bone bolts, intrabody implants, interbody implants, staples, clips, cables, fusion devices, and artificial joint devices, for example. The anchors can be secured to bony tissue, soft tissue, and combinations thereof.

One particular embodiment for proximal portion 12 will be described with reference to FIG. 1, it being understood that it is contemplated that proximal portion 12 can be provided with any mechanism capable of tensioning elongate member 4 in a surgical procedure. Proximal portion 12 provides a tensioning mechanism adapted to apply and maintain tension on elongate member 4 extending through or along tensioning instrument 10 so that a tensioned elongate member 4 can be secured at the surgical site with an anchor, crimp or other suitable fastener.

Proximal portion 12 can include a generally elongated, stepped cylindrical sleeve 20 extending between a distal end 22 and a proximal end 21. Sleeve 20 can include opposing slots 25 in communication with an interior bore 26 extending through proximal portion 12, including sleeve 20. Proximal portion 12 further includes a rack tube 50 having a distal end member 52 and a proximal end member 53. Distal end member 52 is slidably received in bore 26 of sleeve 20, while proximal end member 53 is enlarged relative to distal end member 52. Proximal end member 53 includes a bore therethrough aligned with bore 26 and opening at a proximal end of proximal member 53 to receive a spring housing 48.

Distal end member 52 includes a bottom or first ratchet surface 57 and a side or second ratchet surface 58 extending therealong. First ratchet surface 57 provides a surface by which rack tube 50 can be ratcheted within sleeve 20 for movement proximally relative thereto. Rack tube 50 is telescopically ratcheted with respect to sleeve 20 by utilizing lever actuator 27 which is pivotally mounted between housing side walls 24 with a pivot pin 28. A lever return spring 31 can be attached to sleeve 20 and contact lever actuator 27 to bias lever actuator 27 away from sleeve 20 as shown in FIG. 1. Lever actuator 27 is pivoted about lever pin 28 by pressing handle portion 33 thereof toward sleeve 20 against the bias of spring 31.

Lever actuator 27 is pivotally engaged with a pawl (not shown) mounted to sleeve 20 between walls 24. Lever return spring 31 normally biases the pawl toward engagement with first ratchet surface 57 of rack tube 50. Each depression of actuator lever actuator 27 causes the pawl to move toward proximal end 21 of sleeve 20 and push on one of the adjacent ratchet teeth comprising first ratchet surface 57, thereby moving rack tube 50 proximally relative to sleeve 20. When lever 27 is released, spring 31 biases the distal end of lever 27 away from sleeve 20 and positions the pawl adjacent the next ratchet tooth of first ratchet surface 57. Pressing proximal end 33 of lever actuator 27 again moves the pawl into engagement with the next adjacent ratchet tooth of ratchet surface 57 to move rack tube 50 proximally relative to sleeve 20 in an increment provided by the spacing between the teeth comprising first ratchet surface 57. Further details regarding the operation of tensioning devices can be found, for example, in U.S. Pat. Nos. 5,312,410 and 5,395,374, each of which is incorporated herein by reference in its entirety.

Tensioning instrument 10 also includes a rack lock 40 to lock rack tube 50 from movement distally relative to sleeve 20 upon its movement proximally with lever actuator 27. Rack lock 40 is positioned in a notch 29 formed in sleeve 20 and in communication with distal member 52 of rack tube 50. Rack lock 40 is biased into releasable engagement with one of the adjacent ratchet teeth comprising second ratchet surface 58 along distal member 52 of rack tube 50. Rack lock 40 can be pivoted relative to sleeve 20 and moved to a release position relative to second ratchet surface 58 by depressing release surface 43 toward sleeve 20. Rack lock 40, however, is normally biased so that an engagement member (not shown) on its proximal end is engaged with the second ratchet surface 58. Further details regarding rack lock 40 can be found in the aforementioned '410 and '374 patents.

Proximal member 53 of rack tube 50 provides a cylindrical extension defining a cylindrical cavity opening at its proximal end that slidably receives a spring housing 48. A window 47 can be provided in proximal member 53 that allows viewing of an exterior surface 45 of spring housing 48. Scale markings 41 can be provided in appropriate graduations adjacent window 47. Spring housing 48 includes a reference mark 49 on exterior surface 45 that moves along scale markings 41 as spring housing 48 moves relative to rack tube 50 to provide an indication of the tension force applied to elongate member 4 with tensioning instrument 10.

A proximal end portion 51 of spring housing 48 is provided a cam 55 which is pivotally mounted with a pivot pin 56 in a notch (not shown) formed in proximal end portion 51. Cam 55 includes an elongate member engaging portion (not shown) recessed in the notch and in communication with bore 26 extending through tensioning instrument 10. With elongate member 4 extending through the bore, and with cam 55 in the position shown in FIG. 1, the elongate member engaging portion of cam 55 releasably engages elongate member 4 in the bore of tensioning instrument 10 to secure elongate member 4 relative thereto as it is tensioned. Cam 55 can pinch or press elongate member 4 between its elongate member engaging portion and an inner wall surface of bore 26 along rack tube 50. Thus, as lever 27 is manipulated to move rack tube 50 proximally relative to sleeve 20, elongate member 4 is tensioned since it extends through, but is not engaged to, sleeve 20 but is coupled to rack tube 50 through spring housing 48. The elongate member engaging portion of cam 55 is released from elongate member 4 by pivoting cam 55 in the direction indicated by arrow 59, allowing tensioning instrument 10 to freely slide along elongate member 4.

Figures 2, 3, 4:
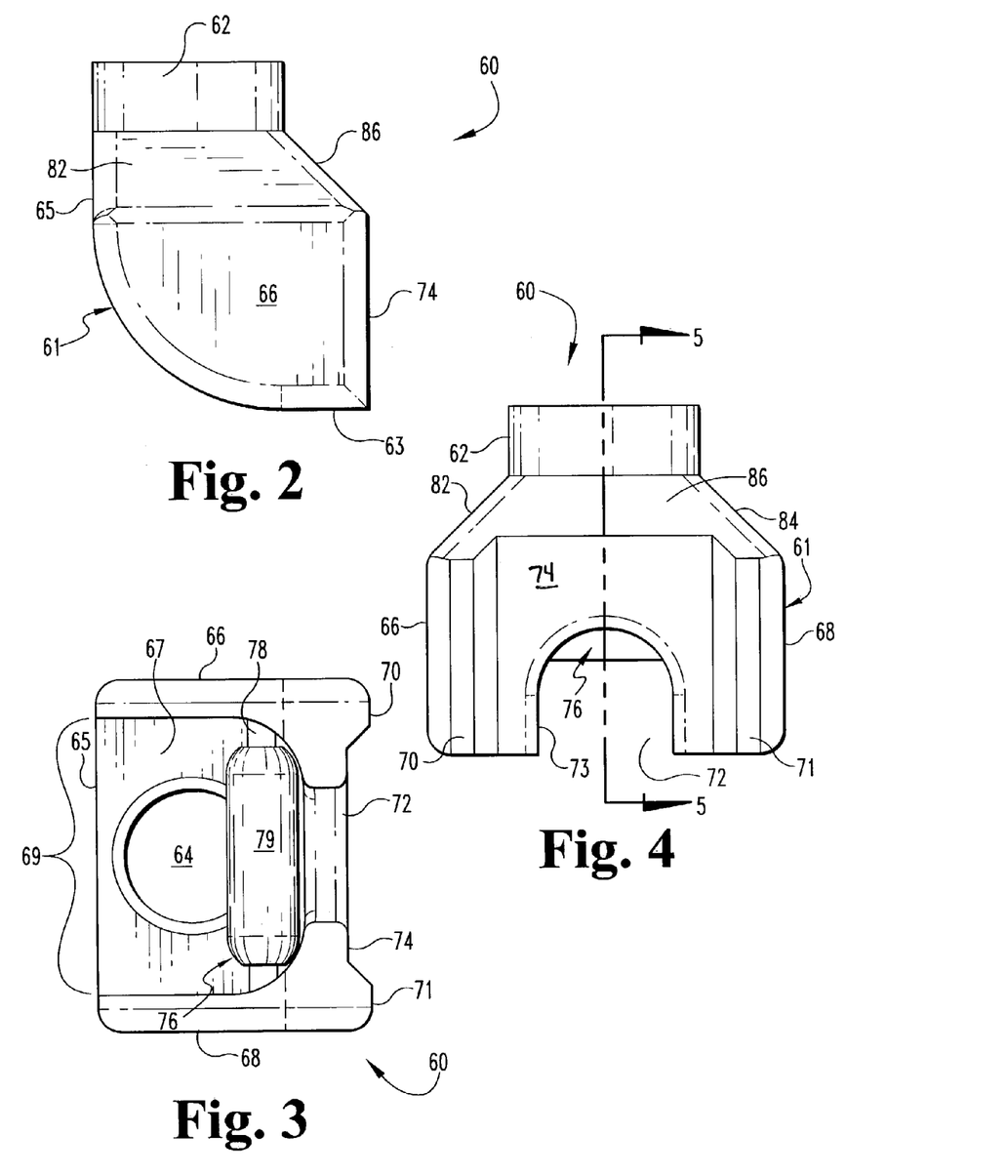
FIG. 2 is an elevation view of a distal end portion of the tensioning instrument of FIG. 1.
FIG. 3 is a bottom plan view of the distal end portion of FIG. 2.
FIG. 4 is a right end view of the distal end portion of FIG. 2.

Referring now to FIGS. 2–4, distal end portion 60 is shown and includes a proximal collar 62 and a housing 61 extending from collar 62 toward a distal end 63. Collar 62 can be attachable to or integrally formed with the distal end of sleeve 20, and includes a bore 64 therethrough in communication with and forming an extension of bore 26. Elongate member 4 is positionable through bore 64 for engagement and tensioning with proximal portion 12.

Housing 61 includes first side wall 66 and an opposite second side wall 68. A first end wall 65 and an opposite second end wall 74 extend between side walls 66, 68. Housing 61 defines a receptacle 67 around which side walls 66, 68 and end walls 65, 74 generally extend. Receptacle 67 is open toward distal end 63. An opening 69 in first end wall 65 is provided in communication with receptacle 67. A passage 72 is provided in second end wall 74 in communication with receptacle 67. Passage 72 is also open toward distal end 63. Receptacle 67 can be sized to receive a structure, such as an anchor or anatomical structure, to facilitate positioning of distal end portion 60 at the desired location at the operative site, as discussed further below.

Distal end portion 60 further includes a support member 76 in receptacle 67 extending between each of the side walls 66, 68 and offset from bore 64 toward second end wall 74. In the illustrated embodiment, support member 76 includes a cylindrical base member 78 fixed to each of the side walls 66, 68 and a tubular roller 79 mounted around base member 78. Other embodiments contemplate other configurations for support member 76. For example, support member 76 can be rotatably mounted to side walls 66, 68. In another example, support member 76 is not rotatable and elongate member 4 slides therealong as it is tensioned with the tensioning mechanism comprising proximal portion 12. Non-tubular and non-cylindrical configurations are also contemplated for support member 76.

Elongate member 4 extends from bore 64 and changes direction relative to proximal portion 12 by contacting support member 76 and extending through passage 72. Support member 76 can be mounted to side walls 66, 68 and offset from the center of bore 64, allowing elongate member 4 to extend through passage 72 and around support member 76 into bore 64 with minimal changes in direction, kinking, or bending of elongate member 4.

Side walls 66, 68 of housing 61 can be provided with flared side wall portions 82, 84 extending distally from collar 62. Second end wall 74 can be provided with a flared wall portion 86 extending from collar 62 to first end wall 74. The flared wall portions separate side walls 66, 68 and end walls 65, 74 from one another to increase the size of receptacle 67. To assist in maintaining the positioning of housing 61 adjacent the proximal end portion of an anchor, abutment members 70, 71 can be provided that extend outwardly from end wall 74 and along each side of passage 72. Abutment members 70, 71 are spaced from another so that the proximal end portion of the anchor can be placed therebetween.

Figure 5:
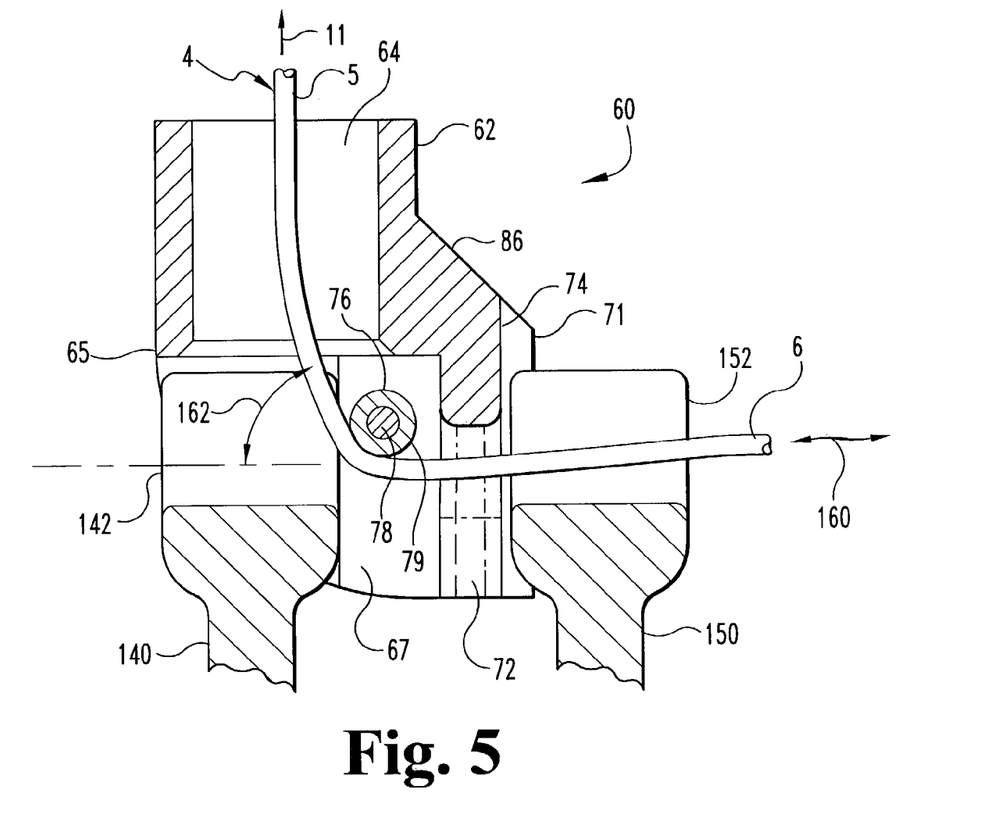
FIG. 5 is a section view through line 5—5 of the distal end portion of FIG. 4 and also including a sectional view of the pair of side by side anchors and a flexible elongate member.

Examples of surgical techniques and applications for distal end portion 60 include surgeries requiring tensioning of elongate member 4 with, for example, a tensioning mechanism such as is provided with proximal portion 12. With reference to FIG. 5, there is shown a first anchor 140 engageable to an anatomical structure and a second anchor 150 engageable to an anatomical structure. Anchors 140, 150 can be engaged to any bony structure or structures, including, for example, the same vertebral body or adjacent vertebral bodies. Tensioning instrument 10 can also have application with anchors engaged to one or more soft tissue structures. Elongate member 4 extends between and can be coupled to one or more of the anchors 140, 150 to interconnect two or more anchors. Elongate member 4 can be provided to stabilize adjacent structures to which anchors 140, 150 are engaged, to secure an anchor to one or more anatomical structures, or to interconnect anchors, for example.

In FIG. 5 end wall 74 of distal end portion 60 is positioned adjacent to proximal end portion 152 of anchor 150. Abutment members 70, 71 extend at least partially around the proximal portion 152, and maintain the lateral positioning of distal end portion 60 relative to anchor 150. Second portion 6 of elongate member 4 extends through proximal portion 152 of anchor 150 to support member 76 as indicated by arrows 160. Elongate member 4 contacts support member 76 so that first portion 5 extends through bore 64 and generally in the direction of longitudinal axis 13 of proximal portion 12 as indicated by arrow 11. Support member 76 provides a smooth transition for elongate member as it changes from the direction indicated by arrows 160 to the direction indicated by arrow 11.

Distal end portion 60 of tensioning instrument 10 includes support member 76 so that tensioning instrument 10 can be oriented transversely to the implantation orientation of elongate member 4 while allowing application of a tensioning force to an elongate member 4 without unduly bending, twisting or kinking or otherwise deforming elongate member 4. Accordingly, second portion 6 of elongate member 4 can extend, for example, from the support member 76 in an implantation orientation between anchors as indicated by arrows 160, and first portion 5 of elongate member 4 can extend transversely to the first portion from support member 76 to the tensioning mechanism, as indicate by arrow 11.

In one application, it is contemplated that first portion 5 of elongate member 4 can be oriented at angle 162 that is substantially perpendicularly to second portion 6 of elongate member 4. Other applications contemplate that the first portion 5 of elongate member 4 can be oriented at angle 162 in the range from 60 degrees to 120 degrees relative to second portion 6. Still other applications contemplate that the first portion 5 of elongate member 4 can be oriented at angle 162 in the range from 45 degrees to 135 degrees relative to second portion 6. Applications are also contemplated where first portion 5 of elongate member 4 can be oriented at angle 162 in the range from 0 degrees to 135 degrees relative to second portion 6. Still further it is contemplated that support member 76 of distal end portion 60 can facilitate orientation of first portion 5 of elongate member 4 at angle 162 relative to second portion 6 at angles approaching 180 degrees during application of a tensioning force with the tensioning mechanism.

Distal end portion 60 facilitates the use of tensioning instrument 10 in surgical applications, for example, where it is desired to tension elongate member 4 through the same access portal in which anchor 150 was positioned. Such an access portal can be formed by a retractor sleeve, a retractor blade, an incision, or other minimally invasive access portal where retraction of tissue and other anatomical structures is minimized. Applications in open and non-minimally invasive surgical procedures are also contemplated.

When the desired tensioning force has been applied to elongate member 4 with tensioning instrument 10, elongate member 4 can be secured to anchor 150 with a set screw cap or other securing device. Examples of suitable anchors and securing devices include those provided in Medtronic Sofamor Danek, Inc.'s CD HORIZON® ECLIPSE™ Spinal System. Other examples of suitable anchors, securing devices and elongate members include those provided in U.S. patent application Ser. No. 10/013,053, which is incorporated herein by reference in its entirety.

To facilitate use in procedures in which anchors 140, 150 are positioned in close proximity to one another, distal end portion 60 is provided with receptacle 67 that is sized to at least partially receive, for example, proximal portion 142 of anchor 140. Distal end portion 60 can be positioned about proximal portion 142 of anchor 140, or about an anatomical structure. Receptacle 67 allows distal end portion 60 to be positioned adjacent anchor 150 for the application of a tensioning force to elongate member 4 even if the proximity of anchor 140 or other structure to anchor 150 would otherwise interfere with such positioning.

In the illustrated embodiment, distal end portion 60 has been shown with receptacle 67 that opens at first end wall 65 and distal end 63. Other embodiments of distal end portion 60 contemplate that opening 69 in end wall 65 is not provided. Distal end portion 60 can be positioned on or against a structure at the surgical site, assisting the surgeon in maintaining the position of tensioning instrument 10 during application of a tensioning force.

In spinal surgeries, tensioning instruments of the present invention can have application in procedures in which anchors are engaged to bony tissue of one or more vertebral bodies and interconnected by one or more flexible elongate members 4. The anchors and elongate members can be implanted by the surgeon for the correction of spinal deformities, in spinal fusion procedures, in the temporary or permanent rigid fixation of bony structures, the temporary or permanent flexible fixation of bony structures, as a buttress for bone grafting techniques for the spine, and in fusionless scoliosis surgery, for example.

A wide variety of surgical approaches and techniques for accessing the spinal column may be used in securing anchors to vertebral bodies and connecting flexible members to the anchors. Such techniques include open surgical techniques in which skin and tissue are retracted to expose the spinal column, endoscopic techniques, and micro-surgical techniques through incisions, for example. The surgical approach may also be any one or combination of anterior, lateral, posterior, postero-lateral, or antero-lateral approaches to the spinal column. It is further contemplated that the surgical approach can be to any portion of the spinal column, including the cervical, thoracic, lumbar and/or sacral regions.

The tensioning instruments of the present invention can be used for the correction or treatment of a spinal deformity or condition through tensioning and attachment of a flexible elongate member to one or more vertebrae along the affected segment of the spinal column. Examples of suitable flexible elongate members include, but are not limited to, cables, artificial strands, rods, artificial ligaments, and combinations thereof. Such constructs can be rigid, semi-rigid, flexible, partially flexible, resorbable, non-resorbable, superelastic, or include shape-memory material. The flexible elongate member can include those that are looped, single strand, multiple strands, braided, or combinations thereof. Materials for the flexible elongate member can include but are not limited to polymers, including polyester and polyethylene; superelastic metals, including nitinol; shape memory alloy, including nickel titanium; resorbable synthetic materials, including suture material, metals, including stainless steel and titanium; synthetic materials, allograft material; and bioelastomer material. The flexible elongate members can be fixably or movably connected to anchors. It is further contemplated that the flexible elongate members can have a fixed length between anchors, a variable length, or combinations of fixed and variable lengths between anchors. Such fixed and/or variable length elongate members can be provided with any combination of constrained, semi-constrained, or unconstrained connections with each anchor.

One specific application of the present invention will now be described with respect to fusionless treatment of scoliosis. Such treatment is provided by attaching a flexible elongate member to anchors engaged to the vertebral bodies on the convex side of the spine. The flexible elongate member can correct, arrest or at least minimize growth on the convex or "long" side of the spine, thereby allowing the concave or "short" side of the spine to grow and catch up with the long side. Alternatively, fusionless tethering may treat abnormal spinal alignment by simply preventing further misalignment such as curve progression.

Figure 6:
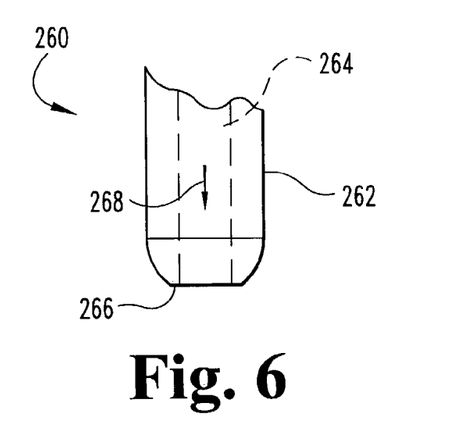
FIG. 6 is an elevation view of another embodiment distal end portion for a tensioning instrument.
Figure 7:
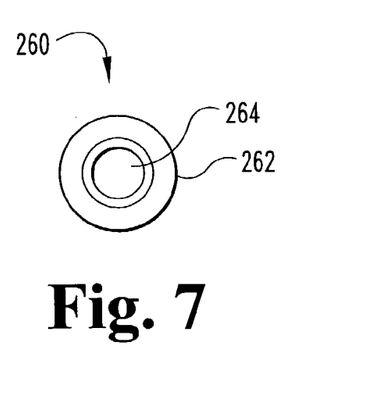
FIG. 7 is an end view of the distal end portion of FIG. 6.

Another embodiment distal end portion 260 for a tensioning instrument is shown in FIGS. 6 and 7. Distal end portion 260 includes a housing 262 having a bore 264 extending therethrough. Bore 264 opens at distal end 266. Distal end 266 of housing 262 includes a semi-spherical shape extending proximally from distal end 266 that facilitates bending of an elongate member extending through bore 264 in a direction transverse to arrow 268 as it exits distal end 266 of housing 262. Distal end portion 260 can be employed at the distal end of a tensioning mechanism that is positioned along an approach to the elongate member that is transverse to the direction in which the elongate member extends at the surgical site.

Figure 8:
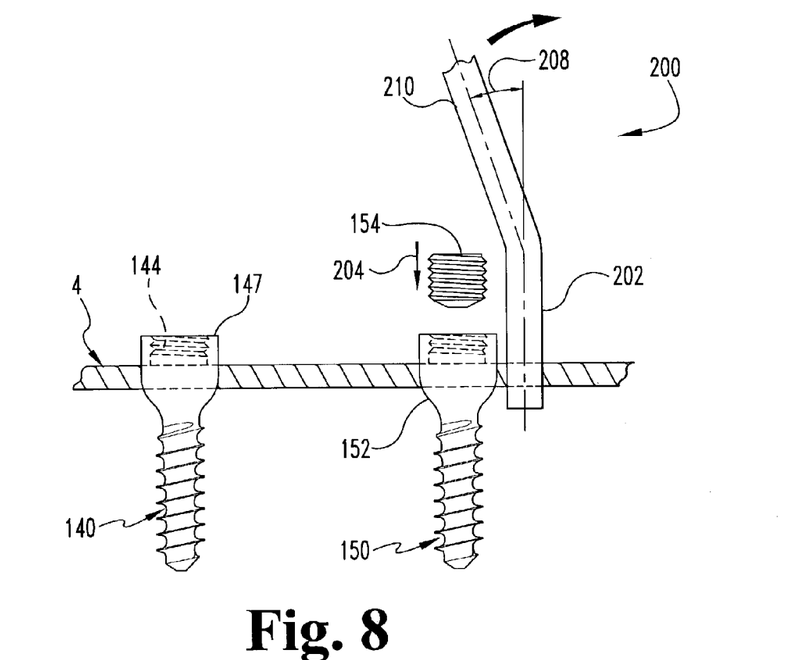
FIG. 8 is an elevation view of another embodiment system for tensioning an elongate member.

FIG. 8 shows another system and technique for tensioning an elongate member in a minimally invasive approach to a surgical site. Anchors 140, 150 are engaged to bony structure, and elongate member 4 extends through the proximal portions 142, 152 of anchors 140, 150. A cap 144 secures elongate member in anchor 140. A tensioning lever 200 is engaged to elongate member 4 adjacent anchor 150. Tensioning lever 200 includes an engaging portion 202 for releasably engaging elongate member 4 and a proximal portion 210. Proximal portion 210 can be angled relative engaging portion 202 as indicated by angle 208 between the central longitudinal axes of portions 202, 210. Elongate member 4 can be tensioned by engaging elongate member 4 with engaging portion 202 and pivoting tensioning lever 200 as indicated by arrow 206 to push engaging portion 202 against proximal portion 152 of anchor 150. The tensioned elongate member 4 can be secured to anchor 150 with cap 154 to maintain the tensile force applied thereto when lever 200 is released.

Figure 9:
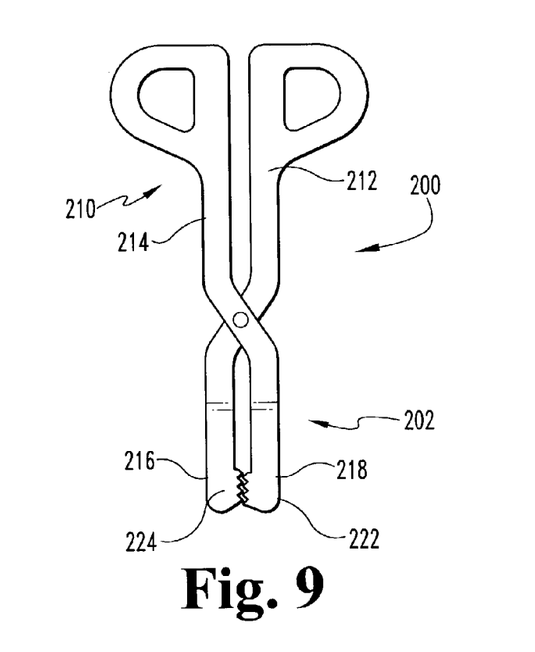
FIG. 9 is another elevation view of an instrument shown in part in FIG. 8.

As shown in FIG. 9, one embodiment for tensioning lever 200 includes a proximal portion 210 that includes a first handle 212 and a second handle 214 pivotally coupled to one another. Engaging portion 202 includes a first arm 216 extending from first handle 212 and a second arm 218 extending from second handle 214. A first engaging member 224 is located at the distal end of first arm 216, and a second engaging member is located at the distal end of second arm 218. Arms 216, 218 can be moved toward one another with handles 212, 214 so that engaging members 224, 222, respectively, engage elongate member 4 therebetween. The angled proximal portion 210 minimizes the amount of tissue retraction required to accommodate the pivoting movement of tensioning lever 200 at the operative site.

While the invention has been illustrated and described in detail in the drawings and foregoing description, the same is to be considered as illustrative and not restrictive in character. All changes and modifications that come within the spirit of the invention are desired to be protected.

What is claimed is:

1. An instrument for tensioning a flexible elongate member in a surgical procedure, comprising:
   a tensioning mechanism engageable to the flexible elongate member and operable to apply a tensioning force thereto; and
   a distal end portion at a distal end of said tensioning mechanism including a receptacle opening at a distal end of said distal end portion and said opening extending from said distal end along at least one side of said distal end portion, said receptacle being sized to at least partially receive a structure at the surgical site when said distal end portion is positioned at the surgical site, wherein said distal end portion includes a support member and during application of the tensioning force a portion of the elongate member extending from the distal end portion is orientable in a first direction for implantation and the elongate member contacts said support member for orientation of a second portion of the elongate member in a second direction along said tensioning mechanism.

2. The instrument of claim 1, wherein said first direction is substantially perpendicular to said second direction.

3. The instrument of claim 1, wherein said distal end portion includes a housing and said support member is rotatable within said housing.

4. The instrument of claim 1, wherein said distal end portion includes a housing, said housing including a bore through which the elongate member extends to said tensioning mechanism, said housing further including a passage through which the elongate member extends from the support member in said first direction.

5. The instrument of claim 4, wherein said passage includes a U-shape opening at a distal end of said housing.

6. The instrument of claim 1, wherein said distal end portion includes a housing and said receptacle opens along a first end wall of said housing opposite a second end wall of said housing.

7. The instrument of claim 6, wherein said second end wall includes a passage through which the elongate member extends.

8. An instrument for tensioning a flexible elongate member in a surgical procedure, comprising:
   a tensioning mechanism engageable to the flexible elongate member and operable to apply a tensioning force thereto; and
   a distal end portion at a distal end of said tensioning mechanism including a receptacle opening at a distal end of said distal end portion and said opening extending from said distal end along at least one side of said distal end portion, said receptacle being sized to at least partially receive a structure at the surgical site when said distal end portion is positioned at the surgical site, wherein said distal end portion includes a housing, said housing including opposite end walls extending between opposite side walls, said end walls and said side walls extending about said receptacle, at least one of said end walls including a passage in communication with said receptacle and said at least one end wall includes a pair of abutment members extending outwardly therefrom, said abutment members being spaced from one another along opposite sides of said passage.

9. An instrument for tensioning a flexible elongate member in a surgical procedure, comprising:
   a tensioning mechanism engageable to the flexible elongate member and operable to apply a tensioning force thereto; and
   a distal end portion at a distal end of said tensioning mechanism including a receptacle opening at a distal end of said distal end portion and said opening extending from said distal end alone at least one side of said distal end portion, said receptacle being sized to at least partially receive a structure at the surgical site when said distal end portion is positioned at the surgical site, wherein said distal end portion includes a housing, said housing including opposite end walls extending between opposite side walls, said end walls and said side walls extending about said receptacle, at least one of said end walls including a passage in communication with said receptacle and said housing include a bore extending proximally therethrough in communication with said receptacle, said housing further including a support member offset from said bore toward said at least one end wall.

10. An instrument for tensioning a flexible elongate member in a surgical procedure, comprising:
    a tensioning mechanism engageable to the flexible elongate member and operable to apply a tensioning force thereto; and
    a distal end portion at a distal end of said tensioning mechanism including a receptacle opening at a distal end of said distal end portion and said opening extending from said distal end along at least one side of said distal end portion, said receptacle being sized to at least partially receive a structure at the surgical site when said distal end portion is positioned at the surgical site, wherein said distal end portion includes a housing, said housing including:
    a collar;
    opposite end walls extending distally from said collar;
    opposite side walls extending distally from said collar and between said opposite end walls; and
    at least one of said end walls and said opposite side walls each including a flared wall portion to separate said at least one end wall and said opposite side walls from one another, said receptacle being defined at least in part by said separated end wall and opposite side walls.

11. The instrument of claim 10, wherein said collar includes a bore in communication with said receptacle, the elongate member extendable through said bore to said tensioning mechanism.

12. An instrument for tensioning a flexible elongate member in a surgical procedure, comprising:
    a tensioning mechanism engageable to a first portion of the elongate member and operable to apply a tensioning force to the elongate member; and
    a distal end portion at a distal end of said tensioning mechanism, said distal end portion including a support member contactable with the elongate member to orient said tensioning mechanism in a first direction relative to a second portion of the elongate member extending distally from the tensioning mechanism in a second direction that is transverse to said first direction.

13. The instrument of claim 12, wherein said distal end portion includes a housing, said housing including opposite side walls, said support member extending within said housing between said side walls.

14. The instrument of claim 13, wherein said support member is rotatable relative to said housing.

15. The instrument of claim 13, wherein said support member includes a base member fixed to said side walls and a roller rotatably mounted about said base member.

16. The instrument of claim 12, wherein said first direction is substantially perpendicular to said second direction.

17. The instrument of claim 12, wherein said first direction is oriented in the range from 60 degrees to 120 degrees relative to said second direction.

18. The instrument of claim 12, wherein said first direction is oriented in the range from 45 degrees to 135 degrees relative to said second direction.

19. The instrument of claim 12, wherein said first direction is oriented in the range from 0 degrees to 135 degrees relative to said second direction.

20. The instrument of claim 12, wherein said distal end portion includes a housing and said support member is positioned in said housing, said support member extending transversely to said first direction and said second direction.

21. The instrument of claim 20, wherein said housing includes a pair of opposite end walls, at least one of said end walls including a passage through which the second portion of the elongate member extends.

22. The instrument of claim 21, wherein said passage is U-shaped and opens at a distal end of said housing.

23. The instrument of claim 20, wherein said housing defines a receptacle opening at a distal end of said housing, said receptacle being sized to at least partially receive a structure at a surgical site when said distal end portion is positioned adjacent the surgical site.

24. The instrument of claim 12, wherein said distal end portion includes a receptacle and a passage in communication with said receptacle and through which the second portion of the elongate member extends, said passage being proximal of a distal end of said distal end portion.

25. The instrument of claim 12, wherein said support member is rotatable about an axis transversely oriented to the elongate member.

26. An instrument for tensioning a flexible elongate member in a surgical procedure, comprising:
a tensioning mechanism engageable to a portion of the flexible elongate member and operable to apply a tensioning force to the elongate member; and
a distal end portion at a distal end of said tensioning mechanism, said distal end portion including a housing and a support member within said housing contactable with the elongate member to change an orientation of the portion of the elongate member engaged with said tensioning mechanism relative to a portion of the elongate member extending from said housing from said support member.

27. The instrument of claim 26, wherein said support member is rotatable relative to said housing about an axis that is transversely oriented to the elongate member in contact therewith.

28. The instrument of claim 26, wherein said housing includes a pair of side walls and said support member extends between said side walls.

29. The instrument of claim 26, wherein said housing defines a bore through which the elongate member extends for engagement with said tensioning mechanism, said support member being offset from said bore in said housing.

30. The instrument of claim 26, wherein said housing defines a passage through which the portion of the elongate member extends, said passage being proximal of said distal end of said housing.

31. The instrument of claim 30, wherein said passage is formed in an end wall of said housing.

32. The instrument of claim 31, wherein said passage is U-shaped and opens at a distal end of said housing.

33. The instrument of claim 26, wherein said distal end portion includes a receptacle with said support member in said receptacle, said distal end portion further including a passage in communication with said receptacle and through which the second portion of the elongate member extends, said passage being proximal of a distal end of said distal end portion.

34. An instrument for tensioning a flexible elongate member in a surgical procedure, comprising:
a tensioning mechanism engageable to the flexible elongate member and operable to apply a tensioning force thereto; and
a distal end portion at a distal end of said tensioning mechanism including a receptacle opening at a distal end of said distal end portion and said opening extending from said distal end along at least one side of said distal end portion, said receptacle being sized to at least partially receive a structure at the surgical site when said distal end portion is positioned at the surgical site, wherein said distal end portion includes a support member in contact with the elongate member, said support member being rotatable about an axis transversely oriented to the elongate member.

35. The instrument of claim 34, wherein said distal end portion includes a passage in communication with said receptacle and through which a distal portion of the elongate member extends, said passage being proximal of said distal end of said distal end portion.

* * * * *